US007027866B2

(12) United States Patent
Warkentin

(10) Patent No.: US 7,027,866 B2
(45) Date of Patent: Apr. 11, 2006

(54) MECHANICALLY-BASED INTERVAL OPTIMIZATION FOR A BIVENTRICULAR PACING ENGINE

(75) Inventor: Dwight H. Warkentin, Arden Hills, MN (US)

(73) Assignee: Medtronic, Inc., Minneapolis, MN (US)

( * ) Notice: Subject to any disclaimer, the term of this patent is extended or adjusted under 35 U.S.C. 154(b) by 76 days.

(21) Appl. No.: 10/629,075

(22) Filed: Jul. 29, 2003

(65) Prior Publication Data

US 2005/0027322 A1    Feb. 3, 2005

(51) Int. Cl.
*A61N 1/365* (2006.01)

(52) U.S. Cl. ...................................... 607/23

(58) Field of Classification Search ............ 607/9, 607/15, 17, 23, 27, 62
See application file for complete search history.

(56) References Cited

U.S. PATENT DOCUMENTS

| 3,937,226 | A |   | 2/1976  | Funke            |
|-----------|---|---|---------|------------------|
| 4,088,140 | A |   | 5/1978  | Rockland et al.  |
| 4,332,259 | A |   | 6/1982  | McCorkle, Jr.    |
| 4,354,497 | A |   | 10/1982 | Kahn             |
| 4,458,677 | A |   | 7/1984  | McCorkle, Jr.    |
| 4,548,203 | A |   | 10/1985 | Tacker, Jr. et al.|
| 4,553,436 | A | * | 11/1985 | Hansson ........ 73/514.33 |
| 4,928,688 | A |   | 5/1990  | Mower            |
| 5,174,289 | A |   | 12/1992 | Cohen            |
| 5,267,560 | A |   | 12/1993 | Cohen            |
| 5,368,040 | A |   | 11/1994 | Carney           |
| 5,403,356 | A |   | 4/1995  | Hill et al.      |
| 5,417,717 | A |   | 5/1995  | Salo et al.      |
| 5,487,752 | A |   | 1/1996  | Salo et al.      |
| 5,514,161 | A |   | 5/1996  | Limousin         |
| 5,540,727 | A |   | 7/1996  | Tockman et al.   |
| 5,564,434 | A |   | 10/1996 | Halperin et al.  |
| 5,584,867 | A |   | 12/1996 | Limousin et al.  |
| 5,626,623 | A |   | 5/1997  | Kieval et al.    |
| 5,674,259 | A |   | 10/1997 | Gray             |
| 5,720,768 | A |   | 2/1998  | Verboven-Nelissen |
| 5,792,203 | A |   | 8/1998  | Schroeppel       |
| 5,797,970 | A |   | 8/1998  | Pouvreau         |

(Continued)

OTHER PUBLICATIONS

Baig et al., "The Hemodynamics of Cardiac Pacing: Clinical and Physiological Aspects", *Progress in Cardiovascular Diseases*, vol. XXXIII, No. 5, pp. 283-298, (Mar./Apr. 1991).

(Continued)

*Primary Examiner*—Kennedy Schaetzle
(74) *Attorney, Agent, or Firm*—Paul H. McDowall; Daniel G. Chapik; Girma Wolde-Michael

(57) ABSTRACT

According to the present invention, discrete measurements of fluid pressure development (and derivatives thereof) are used in optimizing hemodynamics for cardiac resynchronization therapy (CRT) delivery and multiple chamber cardiac pacing, and in enhancing hemodynamics in the event of a sub-optimal left-side lead placement. For example, such diverse pressure measurements include: maximum positive or negative dP/dt values, ePAD, RV systolic, RV diastolic, pulse pressure, and the like. According to the present invention, on a periodic basis or upon demand one or more cardiac pacing intervals are iteratively cycled through a predetermined range and the resulting pressure measurements stored for comparison. The cardiac pacing intervals are then adjusted based at least in part upon the most appropriate, or desirable, measured hemodynamics of the patient. The present invention may be implemented as computer readable instructions executed by a microprocessor-based implantable medical device.

17 Claims, 6 Drawing Sheets

U.S. PATENT DOCUMENTS

| | | | |
|---|---|---|---|
| 5,800,464 A * | 9/1998 | Kieval | 607/9 |
| 5,836,987 A | 11/1998 | Baumann et al. | |
| 5,902,324 A | 5/1999 | Thompson et al. | |
| 6,026,324 A * | 2/2000 | Carlson | 607/27 |
| 6,044,298 A | 5/2000 | Salo et al. | |
| 6,058,329 A | 5/2000 | Salo et al. | |
| 6,070,100 A | 5/2000 | Bakels et al. | |
| 6,129,744 A | 10/2000 | Boute | |
| 6,144,880 A | 11/2000 | Ding et al. | |
| 6,171,252 B1 | 1/2001 | Roberts | |
| 6,221,024 B1 | 4/2001 | Miesel | |
| 6,285,907 B1 | 9/2001 | Kramer et al. | |
| 2003/0004548 A1 | 1/2003 | Warkentin | |

OTHER PUBLICATIONS

Cazeau et al., "Four Chamber Pacing in Dilated Cardiomyopathy", *PACE*, vol. 17, Part II, pp. 1974-1979, (Nov. 1994).

Daubert et al., "Permanent Dual Atrium Pacing in Major Intra-atrial Conduction Blocks: A Four Years Experience", *PACE*, vol. 16, Part II, pp. 885, (Apr. 1993).

Daubert et al., "Permanent Left Ventricular Pacing With Transvenous Leads Inserted Into The Coronary Veins", *PACE*, vol. 21, Part II, pp. 239-245, (Jan. 1998).

Daubert et al., "Renewal of Permanent Left Atrial Pacing via the Coronary Sinus", *PACE*, vol. 15, Part II, pp. 572, (Apr. 1992).

Kass et al., "Improved Left Ventricular Mechanics From Acute VDD Pacing in Patients With Dilated Cardiomyopathy and Ventricular Conduction Delay", *Circulation*, pp. 1567-1573 (Mar. 30, 1999).

* cited by examiner

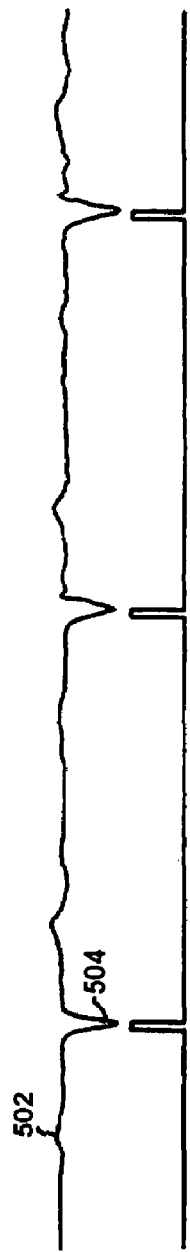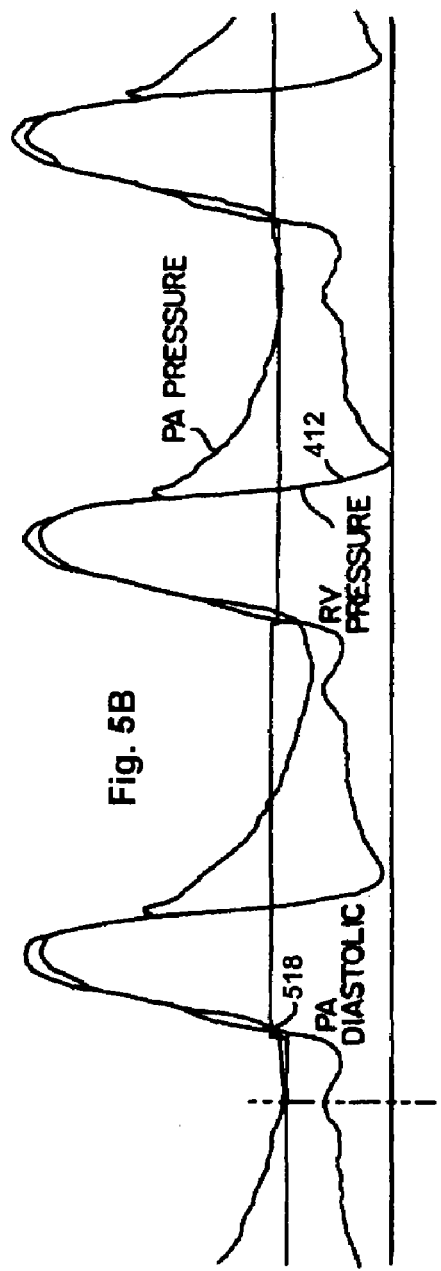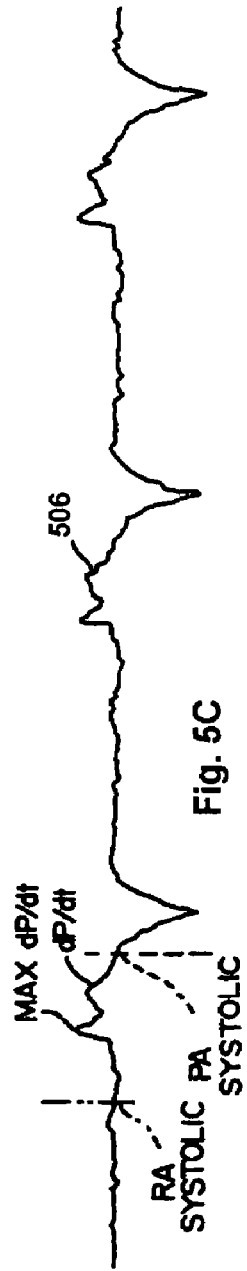

MECHANICALLY-BASED INTERVAL OPTIMIZATION FOR A BIVENTRICULAR PACING ENGINE

CROSS REFERENCE TO RELATED APPLICATION

The present invention relates non-provisional U.S. application Ser. No. 10/629,424 entitled, "Apparatus and Method for Hemodynamics-Based Optimization of Cardiac Pacing," invented by Kjellstrom et al, and filed on common date herewith, the contents of which are hereby incorporated by reference herein.

FIELD OF THE INVENTION

The present invention pertains to multi-site ventricular pacing systems, and particularly bi-ventricular and AV synchronous cardiac pacing systems that pace and sense in at least one atrial heart chamber and deliver ventricular pacing pulses to both right ventricular (RV) and left ventricular (LV) sites. The present invention pertains to hemodynamically-based optimized pacing intervals for cardiac resynchronization therapy (CRT) delivery. In general, the present invention provides a method of closed-loop control for a bi-ventricular pacing engine based on measurements of pressure developed (and mathematical derivatives and/or integrals thereof) during iterative adjustment of one or more pacing intervals to determine a hemodynamically preferred combination of pacing intervals.

BACKGROUND OF THE INVENTION

When functioning properly, the human heart maintains its own intrinsic rhythm and will pump an adequate supply of blood throughout the body's circulatory system. However, some people have cardiac arrhythmias that result in diminished blood circulation. One method of treating cardiac arrhythmias is the administration of drug therapy. Another method is the use of a cardiac rhythm management system. Such systems (pacers, cardioverters, among others) are usually implanted in the patient and deliver electrical stimulation therapy directly to the heart.

One type of cardiac disturbance faced by cardiac rhythm management systems is congestive heart failure (CHF). CHF, which can result from long-term hypertension, is a condition in which the muscles in the walls of the right and/or left sides of the heart are stretched abnormally with each cardiac filling and contraction. As a result, the left atrium and left ventricle become enlarged, and the heart muscle possesses less contractility, a condition called left ventricular dysfunction (LVD). LVD decreases cardiac output, which, in turn, often results in an increased heart rate with less resting time between contractions. The heart consumes more oxygen, and its condition, along with the patient's, typically worsens over a period of time.

When the left side of the heart has become enlarged due to CHF, the ventricular depolarization signals may travel through and depolarize the left side of the heart more slowly than they do in the right ventricle. As a result, the left and right ventricles do not contract simultaneously. Rather, the left ventricle contracts somewhat later than the right ventricle. This further reduces the pumping efficiency of the heart. Furthermore, significant conduction disturbances between the right and left atria can result in left atrial flutter or fibrillation, further reducing the pumping efficiency of the heart.

As a result, there has been a need to provide CHF patients with a pacing therapy that coordinates ventricular contractions or otherwise increases the heart's pumping efficiency. Most recently, biventricular synchronous pacing that provides pacing pulses to both right and left ventricles has met this need.

In general, conduction disturbances in LVD patients benefit from pacing pulses applied at multiple electrode sites positioned in or about a single heart chamber or in both right and left heart chambers. These pacing pulses may also be delivered in synchrony with paced or sensed depolarizations detected at one of the electrode sites. Atrial and left ventricular cardiac output can be significantly improved when left and right chamber synchrony is restored, particularly in patients suffering from dilated cardiomyopathy, LVD and CHF.

A number of proposals have been advanced for providing pacing therapies to restore synchronous depolarization and contraction of a single heart chamber and the like as described in detail in the commonly assigned U.S. Pat. No. 6,129,744 and in commonly assigned U.S. Pat. Nos. 5,626,623, 5,403,356, 5,797,970, 5,902,324, and 6,070,100 and in U.S. Pat. Nos. 5,720,768 and 5,792,203 the contents of each patent is hereby incorporated by reference herein. The proposals appearing in U.S. Pat. Nos. 3,937,226, 4,088,140, 4,548,203, 4,458,677, 4,332,259 are summarized in U.S. Pat. Nos. 4,928,688 and 5,674,259. The advantages of providing sensing at pace/sense electrodes located in both the right and left heart chambers is addressed in the '688 and '259 patents, as well as in U.S. Pat. Nos. 4,354,497, 5,174,289, 5,267,560, 5,514,161, and 5,584,867. The art has recently turned its attention to the duration of A-V and/or V-V intervals to improve biventricular pacing. In U.S. Pat. No. 6,144,880, to Ding et al. purportedly describe multiple ways to provide optimized timing for ventricular pacing by determining certain intrinsic electrical or mechanical events in the atria or ventricles that have a predictable timing relationship to the delivery of optimally timed ventricular pacing that maximizes ventricular performance. This patent purportedly discloses methods to predict AV intervals for use in biventricular pacing based on numerous tests and experiments to measure hemodynamic parameters, from which generic algorithms were developed that are applied to all patients. These measurements, as the inventors make quite clear, do not use patient-specific measurements of hemodynamic parameters. In U.S. Pat. No. 6,285,907, Kramer et al. purportedly disclose techniques for computing an AV interval in biventricular pacing based on an underlying intrinsic heart rate, the intrinsic AV interval, or sensor indicated rate. The methods proposed in this patent, while they are patient-specific, are not directly derived from the measurement of hemodynamic parameters.

In U.S. Pat. No. 6,804,555 to Warkentin a system and method for monitoring the QRS duration is provided wherein processing QRS duration signals provides data from which the onset or progression of heart failure is determined. In the Warkentin patent, adjusting SAV/PAV delays and/or V-V delays provides a way to improve delivery of synchronous pacing pulses as a function of QRS duration. The SAV/PAV/V-V delays are varied from the prevailing delays as a function of the measured width of the QRS complex. The Warkentin patent was filed 29 Jun. 2001 and is entitled, "Multi-site Venticular Pacing System Measuring QRS Duration," is hereby incorporated by reference herein.

The medical literature also discloses a number of approaches for providing bi-atrial and/or bi-ventricular pacing as set forth in: Daubert et al., "Permanent Dual Atrium Pacing in Major Intra-atrial Conduction Blocks: A Four Years Experience", *PACE* (Vol. 16, Part II, NASPE Abstract 141, p.885, April 1993); Daubert et al., "Permanent Left Ventricular Pacing With Transvenous Leads Inserted Into The Coronary Veins", *PACE* (Vol. 21, Part II, pp. 239–245, January 1998); Cazeau et al., "Four Chamber Pacing in Dilated Cardiomyopathy", *PACE* (Vol. 17, Part II, pp. 1974–1979, November 1994); and Daubert et al., "Renewal of Permanent Left Atrial Pacing via the Coronary Sinus", *PACE* (Vol. 15, Part II, NASPE Abstract 255, p. 572, April 1992).

Kass et al., in "Improved Left Ventricular Mechanics From Acute VDD Pacing in Patients With Dilated Cardiomyopathy and Ventricular Conduction Delay," *Circulation*, (Mar. 30, 1999), report the results of their study of the impact of $dP/dt_{max}$, arterial pulse pressure (PP), and peak-systolic pressure measurements at various pacing sites in VDD pacing, with data at optimized A-V intervals for each site in the tested patients.

With respect to pressure sensing apparatus capable of chronic in vivo operation, many devices and methodologies have been proposed and/or implemented in the prior art. In this regard, the following issued U.S. patents provide added details for several representative pressure monitoring techniques; namely: U.S. Pat. Nos. 5,368,040; 5,564,434; 6,171,252; and 6,221,024 the contents of each are hereby incorporated herein as if fully set forth herein.

SUMMARY OF THE PRESENT INVENTION

In view of the foregoing, the present invention provides a method and apparatus to determine the hemodynamic status of a patient from chronic measurements of pressure obtained from a pressure sensor located in fluid communication with a right ventricular (RV) chamber. Beside direct measurement of RV pressure development, mathematical first and second derivatives and integrals of measured pressure correspond to a better understanding of the hemodynamic status of a patient. For example, estimated pulmonary arterial diastolic (ePAD) pressure can be readily derived from an RV pressure waveform for any given cardiac cycle. The inventor has found that when the dynamic fluid pressure in the RV is measured, a strong correlation exists between said pressure(s) and the degree of heart failure as well as possible non-optimal placement of a pacing lead in the left ventricle (LV). In particular, the inventor has discovered that patients suffering from dilated cardiomyopathy (DCM) and ventricular conduction delay, especially if receiving CRT, stand to benefit from pacing interval-based hemodynamic optimization according to the present invention. The inventive techniques employ continuous and/or periodic monitoring of the RV pressure and measuring RV pressure at the moment of specific events. Further discussion of the use of these measured parameters is found in U.S. Pat. No. 5,368,040 issued to Carney (the '040 patent) and incorporated herein by reference in its totality.

The present invention employs a pressure sensor to chronically measure pressure and periodically record fluid pressure developed in the RV. According to the '040 patent, when an RV pressure sensor signal reaches a local maximum value the time rate-of-change corresponds to a null value. When the positive time rate-of-change ($dP/dt_{max}$) peaks, the pulmonary valve opens and while RV pressure continues to increase, the rate-of-change begins to slow its ascent (a reduced value of dP/dt) until maximum RV pressure develops (when dP/dt=0) before declining. The RV pressure declines abruptly as the chamber empties, and a maximum rate at which RV pressure declines ($dP/dt_{min}<0$) corresponds to a rapidly emptying, or nearly empty, chamber.

According to the present invention, taking diverse pressure measurements (and derivatives thereof) is particularly useful in optimizing CRT delivery and enhancing CRT, especially in the event of a sub-optimal left-side lead placement. For example, such diverse pressure measurements include: maximum positive or negative dP/dt values, ePAD, RV systolic, RV diastolic, pulse pressure, and the like. According to the present invention, on a periodic basis or upon demand the pacing intervals are iteratively cycled through a range and the desired pressure measurements stored. The intervals are then adjusted as a function of optimal, or desirable, hemodynamic response from a patient.

Since the peak rate-of-change of RV pressure provides an indication of the quality of RV chamber filling and systolic function, and the rate is largely governed by temporal pacing intervals (e.g., A-A, A-V, V-A, "sensed-A-V" or SAV, "paced A-V" or PAV, and V-V intervals, among others) the present invention provides for closed-loop hemodynamic-based optimization to enhance a given pacing modality, including CRT. In addition, the present invention provides optimization for sub-optimal left ventricular (LV) lead placement and, thus, enhanced pacing therapy delivery.

Thus, a serial adjustment of a given pacing interval while measuring RV pressure, and derivatives thereof (dP/dt) provides an efficient means to optimize contractile efficiency for a given patient. When attained, the AV interval value that coincides with this measured value is selected as an optimal value and implemented as a part of the timing sequence for a desired cardiac pacing therapy. In the same manner, selection of optimal temporal ventricular pacing stimulation can be used; for example, to enhance delivery of CRT and/or to enhance atrial contribution—as reflected in an increased maximum right ventricular pressure—by comparing different A-A intervals to measured values of ePAD. Such an embodiment of the present invention can enhance the operation of so-called bi-atrial and bi-ventricular, or four-chamber, pacing (4CP) modality.

Automation of the adjustment of the pacing intervals using RV pressure (and derivatives) according to the present invention results in considerable reduction in the time required to hemodynamically optimize therapy. Physicians, clinicians or other medical technicians who follow CHF patients—having three-chamber pacing (3CP) and four-chamber pacing engines (4CP) and other bi-ventricular pacing systems—may thus efficiently serve a larger patient population.

Those of skill in the art will readily appreciate that the present invention may be embodied in executable instructions stored on a computer readable medium operable in an implantable medical device (IMD) such as an implantable pulse generator (IPG), implantable cardioverter-defibrillator (ICD) and the like. Such devices may couple to one or more pressure transducers to receive RV pressure measurements, and calculate derivatives thereof whether such transducers are chronically or acutely implanted. Such implantable devices may have more than one lead per cardiac chamber, although such a configuration is not necessary to practice the present invention.

BRIEF DESCRIPTION OF THE DRAWINGS

FIG. 5A illustrates an actual patient cardiac waveform of an ECG signal.

FIG. 5B illustrates actual patient cardiac waveforms of pulmonary artery pressure and right ventricular pressure signals.

FIG. 5C illustrates a waveform resulting from the derivative (dP/dt) of the right ventricular pressure signal depicted in FIG. 5C.

DETAILED DESCRIPTION OF THE DRAWINGS

Figure 1:
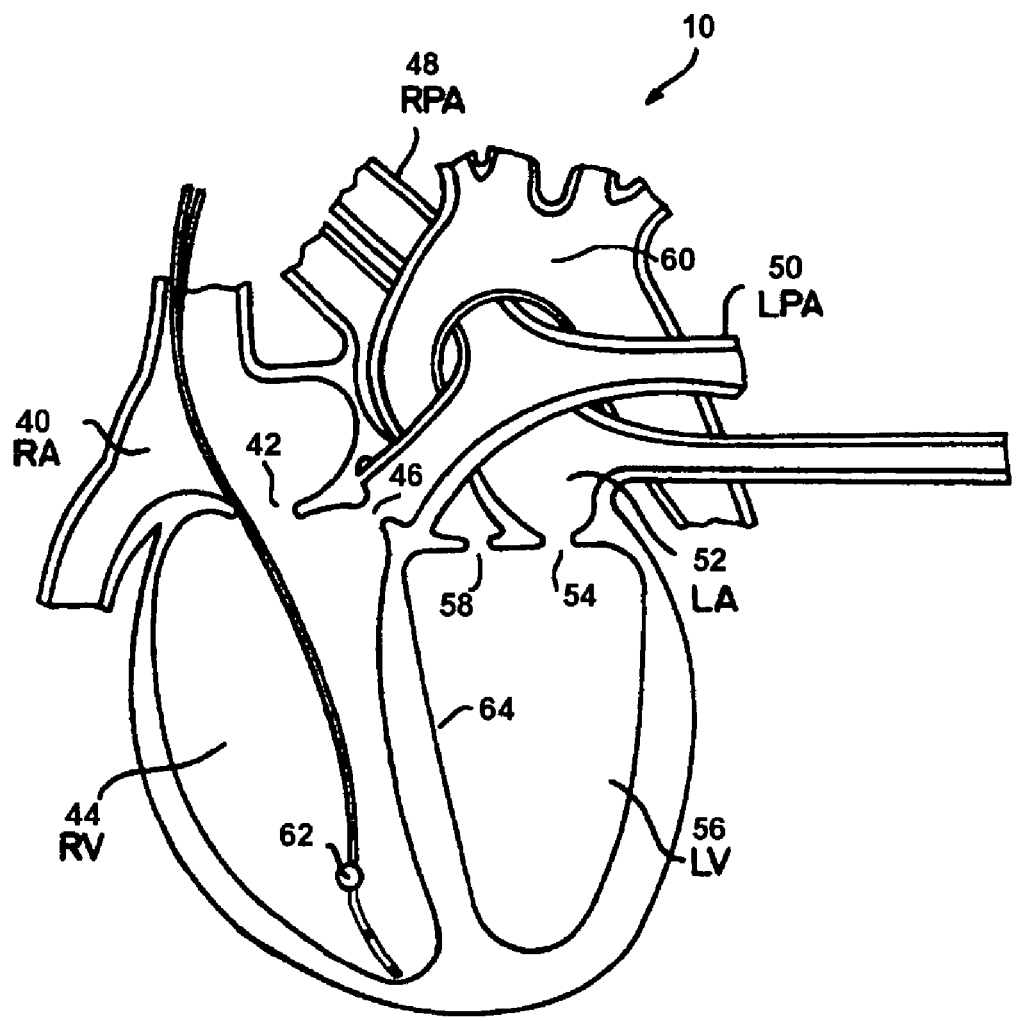
FIG. 1 is a schematic diagram of a human heart showing the various chambers through which the blood flows as well as a pacing lead equipped with a right ventricular pressure sensor.

Turning now to the drawings, FIG. 1 provides a schematic cross-sectional diagram of a human heart 10 from which an understanding of hemodynamic pumping action can be derived. With this background, a better understanding of abnormal cardiac pumping actions, such as CHF and LVD may be gained. A human heart 10 has an intrachamber septum 64 dividing the cardiac chambers on the left side (LA, LV) from the right side (RA, RV). The two atrial chambers 40, 52 each have a valve that allows blood to pass through to the ventricles. The tricuspid valve 42 and mitral valve 54 regulate blood flow between the atrium and the ventricle on each side. As described, when RV pressure reaches a maximum positive rate-of-change pulmonary valve 46 opens to allow venous blood to flow from the RV to the pulmonary arteries 48, 50 which supply blood to the lungs. Aortic valve 58 regulates blood flow from the left ventricle to aorta 60 and to the body.

The circulation of the blood through heart 10 begins on the right side (left side of drawing). Relatively large veins, the superior vena cava and inferior vena cava (not shown) return blood from the body to right atrium 40. This blood then flows through tricuspid valve 42 into right ventricle 44, and leaves right ventricle 44 through pulmonary valve 46 then to the lungs via right 48 and left 50 pulmonary arteries. The two arterial branches carry blood to the right and left lungs (not shown). Oxygenated blood from the lungs reenters the heart 10 flowing into left atrium 52 and passes into left ventricle 56 through mitral valve 54. The blood leaves left ventricle 56 through the aortic valve 58 to enter aorta 60. According to the present invention, a pressure sensor 62 couples to a right ventricular pacing lead 64.

The hemodynamic, or pumping, action of the heart 10 depends almost totally on changes or differences in pressure gradients between the heart's chambers. Cardiac output, the volume of blood ejected from each ventricle during one minute, is the product of heart rate, ejection fraction and stroke volume. Stroke volume is the volume of blood ejected with each heartbeat and depends on preload, myocardial contractility and afterload. Preload refers to the load that stretches the cardiac muscle prior to contraction. The amount of blood in the right ventricle at the end of diastole constitutes preload for the next beat. Right ventricular preload is altered by increasing venous return to the right heart as seen with inspiration and exercise. Conversely, dilated capillary beds and exhalation will decrease venous return. Afterload refers to the resistance against which the ventricle must contract. Resistance can be the result of: thickness and flexibility of the walls of the aorta and large arteries, the peripheral vascular tree, volume of the blood and the viscosity of the blood, among others. Myocardial contractility is the ability of the cardiac muscle to shorten when given a load. Contractility can be increased by the action of the sympathetic nervous system and decreases when the myocardium is damaged. Because of the way the heart depolarizes, events on the left side of the heart typically slightly precede events on the right side. Thus, the mitral valve 54 closes slightly ahead of the tricuspid valve 42 and the aortic valve closes slightly ahead of the pulmonic valve. The staggered closing of the valves produces a splitting of the $S_1$ and $S_2$ heart sounds. Splitting of the second heart sound is exaggerated by inspiration due to the pressure drop in the thoracic cavity. Respiration has little effect on $S_1$ splitting. Normally ventricular systole is slightly shorter than diastole. As heart rate increases, the difference in duration decreases. At about 120 beats per minute, the phase lengthens and becomes nearly equal. Several disorders of the heart have been studied which prevent the heart from operating normally. One such disorder is from degeneration of the LV conduction system, which blocks the propagation of electric signals through some or all of the fast conducting Purkinje fiber network. Portions of the LV that do not receive electrical signals through the fast conducting Purkinje fiber network can only be depolarized through muscle tissue conduction, which is slow and occurs in sequential manner. As a result, the contraction of these portions of the LV occur in stages, rather than synchronously. For example, if the posterior wall of the LV is affected by the conduction disorder, then it contracts later than the septum that is activated through normal conduction. Such asynchronous contraction of the LV walls degrades the contractility (pumping power) of the LV and reduces the LV $dp/dt_{max}$.

If a heart failure patient suffers from another affliction, such as dilated cardiomyopathy (DCM), in addition to conduction disorder(s), hemodynamic inefficiency will likely render the patient symptomatic.

Another disorder of the heart occurs when blood in the LV flows back into the LA, resulting in reduced stroke volume and cardiac output. This disorder is called mitral regurgitation and can be caused by an insufficiency of the mitral valve, a dilated heart chamber (due to DCM), or an abnormal relationship between LV pressure and LA pressure. The amount of the back flow is a complex function of the condition of the mitral valve, the pressure in the LV and in the LA, and the rate of blood flow through the left heart.

These disorders may be found separately or in combination in patients. For example, such disorders are found in patients exhibiting congestive heart failure (CHF). CHF is a disorder of the cardiovascular system. Generally, CHF refers to a cardiovascular condition in which abnormal circulatory congestion exists as a result of inadequate blood flow. Circulatory congestion is a state in which there is an increase in blood volume in the heart but a decrease in the stroke volume. Reduced cardiac output could be due to several disorders, including mitral regurgitation (a back flow of blood from the LV to the LA) and intrinsic ventricular conduction disorder (asynchronous contraction of the ventricular muscle cells), which are the two common abnormalities among CHF patients. When delivering CRT to a patient, it is important to synchronize the systolic contractions of both the right and left sides of the heart. A useful physiologic measurement for ascertaining such synchronized systolic function is fluid pressure developed during delivery of CRT to the patient. As noted herein, measuring pressure developed at discrete moments during a cardiac cycle provides a strong indication of synchronization. The present invention provides for use of direct measurement of RV pressure, derivatives thereof (e.g., $dP/dt_{max/min}$), and, assuming that computational overhead and current drain is not too great, integrals thereof.

PA diastolic pressure is similarly determined from the RV. As long as the PA pressure is higher than the RV pressure, the PA valve is closed. As the ventricle begins to contract during systole, however, the RV pressure surpasses the PA pressure and the PA valve opens. Thus, the pressure in the PA at the time the PA valve opens is the lowest pressure seen by the pulmonary artery and, therefore, corresponds to PA diastolic pressure. Accordingly, the PA diastolic pressure is the pressure in the RV at the moment the PA valve opens. When the PA valve opens has been shown to be nearly identical to the time of maximal positive rate-of-change increase in RV pressure (i.e., $dP/dt_{max}$). The point of $dP/dt_{max}$ is when the PA valve is open and the pressures are equal between the PA and RV and correlates to the so-called estimated pulmonary artery diastolic (ePAD) pressure. Furthermore, pulse pressure (PP) measurements, both direct and via a suitable pressure surrogate, provides an excellent metric upon which hemodynamic optimization may be based.

Figure 2:
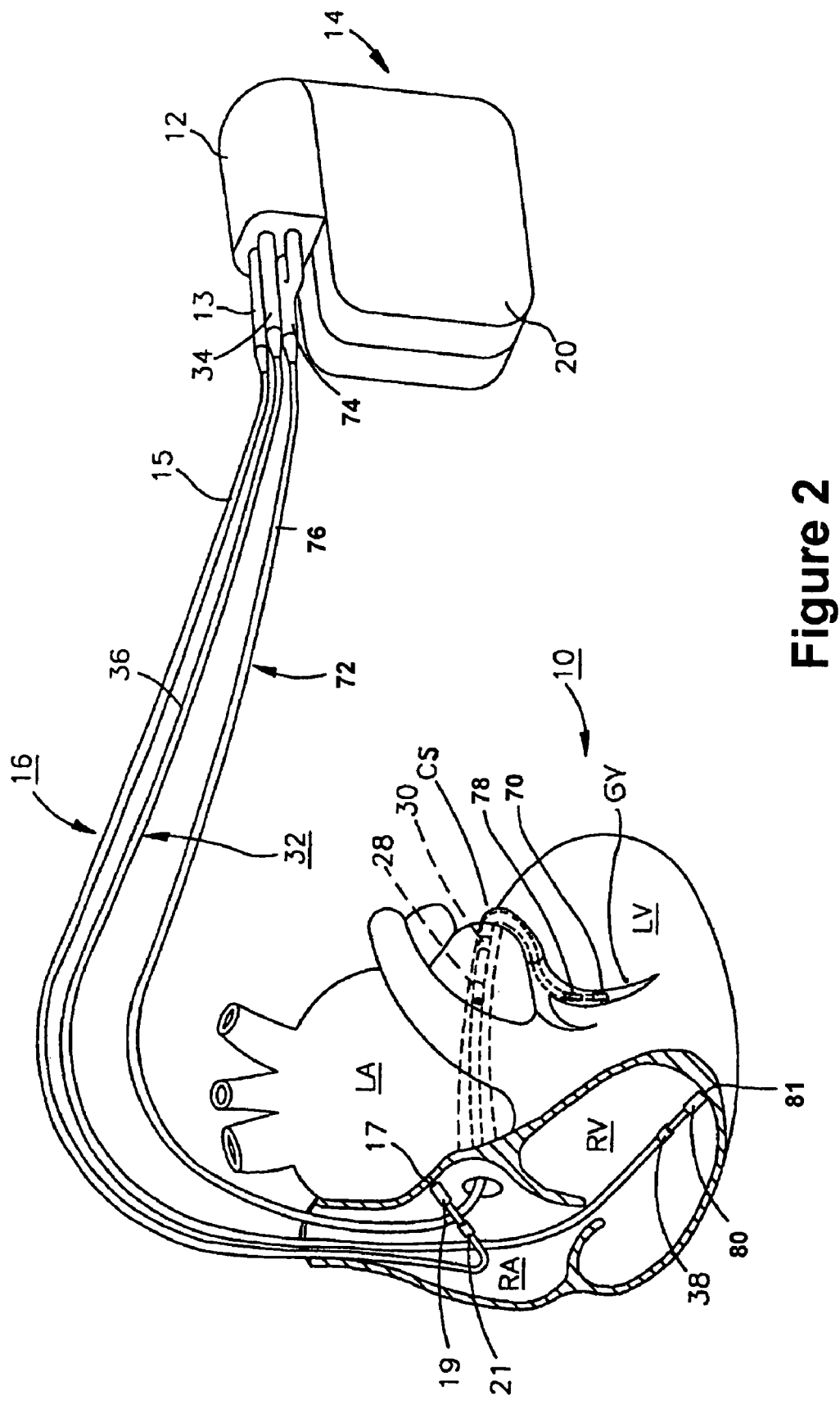
FIG. 2 is a schematic diagram depicting a four channel, bi-atrial and bi-ventricular, pacing system in which the present invention is preferably implemented.

FIG. 2 is a schematic representation of an implanted, three channel (or triple chamber) cardiac pacemaker for restoring synchronous contractions to the atrial and ventricular chambers while also providing simultaneous or sequential pacing to both ventricles. Implantable pulse generator (IPG) 14 is implanted subcutaneously in a patient's body between the skin and the ribs. Three endocardial leads 16, 32 and 72 connect the IPG 14 with the RA, the RV and the LV, respectively, through connections made in the IPG connector block 12. A remote indifferent electrode may be formed as part of the outer surface of housing 20 of IPG 14.

The present invention will be described herein in an embodiment that includes an IPG configured to deliver CRT. Those of ordinary skill in the art, however, with the benefit of the present disclosure will appreciate that the present invention may be advantageously practiced in connection with numerous other types of IMDs such as defibrillators, cardioverters, and the like.

The depicted bipolar endocardial RA lead 16 is passed through a vein into the RA, and the distal end of RA lead 16 is implanted in the RA appendage or fixed to the RA wall by a positive fixation mechanism 17. Bipolar endocardial RA lead 16 is connected via an in-line connector 13 fitting into connector block 12 that is coupled to a pair of electrically insulated conductors within lead body 15 and connected to distal tip RA pace/sense electrode 19 and proximal ring RA pace/sense electrode 21. Delivery of atrial pace pulses and sensing of atrial sense events typically occurs between the distal tip RA pace/sense electrode 19 and proximal ring RA pace/sense electrode 21, wherein the proximal ring RA pace/sense electrode 21 functions as an indifferent electrode.

Alternatively, a unipolar endocardial RA lead could be substituted for the depicted bipolar endocardial RA lead 16 so that sensing occurs between a unipolar RA lead and the (indifferent electrode) housing 20 of IMD 14. Bipolar, endocardial RV lead 32 is passed through a vein and the RA chamber of heart 10 and into the RV where its distal ring and tip RV pace/sense electrodes 38, 80 may be disposed in the apex of the RV by a conventional distal attachment mechanism 81. The RV lead 32 is electrically and mechanically coupled via an in-line connector 34 into a bipolar bore of connector block 12 that is coupled to a pair of electrically insulated conductors within lead body 36 and connected with distal tip RV pace/sense electrode 80 and proximal ring RV pace/sense electrode 38.

In this illustrated embodiment, a bipolar, endocardial coronary sinus (CS) lead 72 is passed through a vein and the RA chamber of the heart 10, into the CS and then inferiorly into a branching vessel of the great vein (GV) to extend the proximal and distal LV CS pace/sense electrodes 78 and 70 alongside the LV chamber. The distal end of such a CS lead is advanced through the superior vena cava, the right atrium, the ostium of the coronary sinus, the coronary sinus (CS), and into a left descending coronary vein, such as the GV.

In a four chamber pacemaker (4CP) embodiment, LV CS lead 52 could bear proximal LA CS pace/sense electrodes 28 and 30 positioned along the CS lead body to lie in the larger diameter CS adjacent the LA. Typically, LV CS leads and LA CS leads do not employ any fixation mechanism and instead rely on the close confinement within these vessels to maintain the pace/sense electrode or electrodes at a desired site. The LV CS lead 72 is formed with a multiple conductor lead body 76 coupled at the proximal end connector 74 fitting into a bore of IPG connector block 12. A small diameter lead body 76 is selected in order to lodge the distal LV CS pace/sense electrode 70 deeply in a vein branching inferiorly from the great vein (GV).

In this case, the CS lead body 56 would encase four electrically insulated lead conductors extending proximally from the more proximal LA CS pace/sense electrode(s) and terminating in a dual bipolar connector 74. The LV CS lead body would be smaller between the LA CS pace/sense electrodes 28 and 30 and the LV CS pace/sense electrodes 78 and 70.

Figure 3:
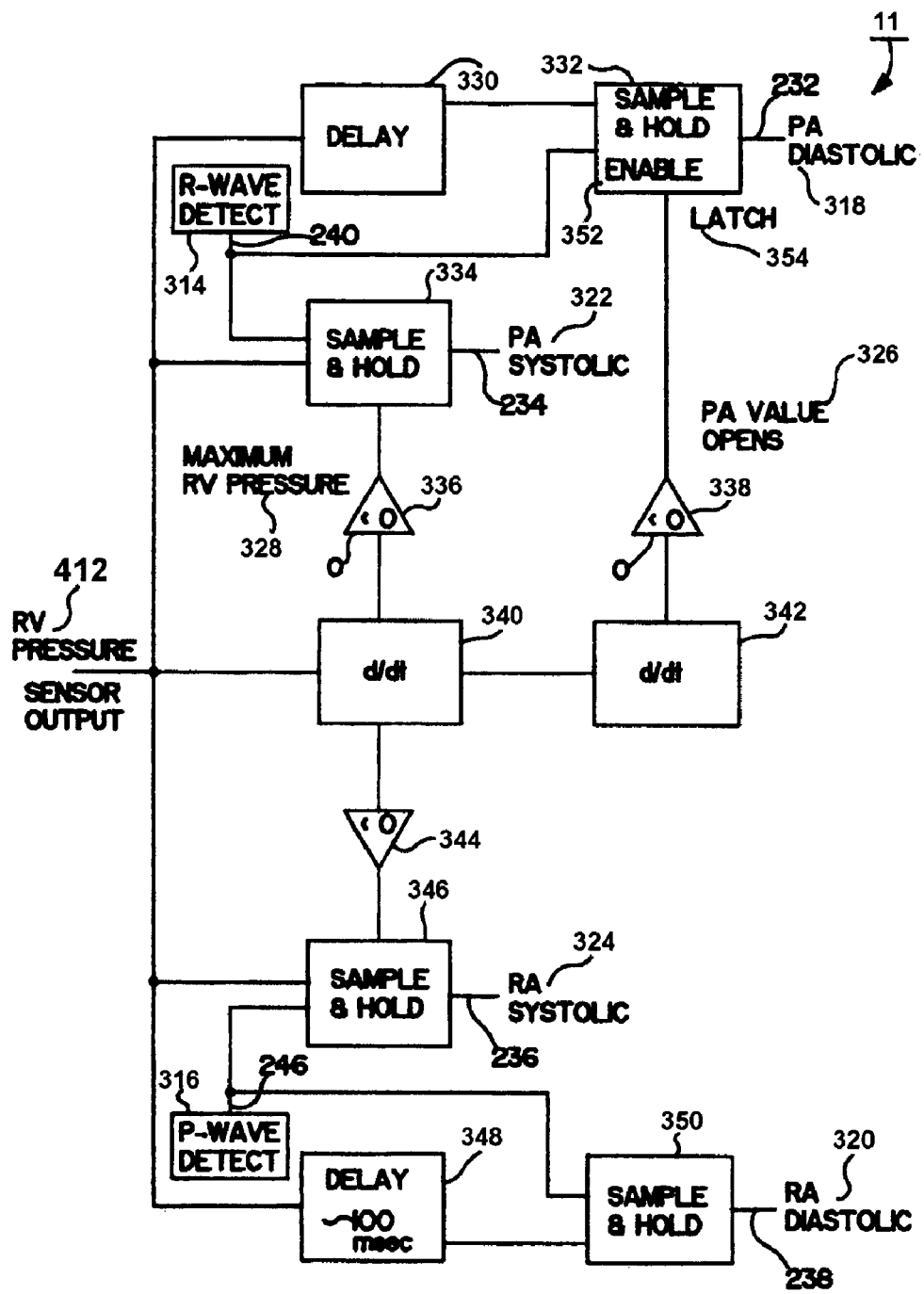
FIG. 3 is a partially block, schematic diagram of a control system, responsive to a right ventricular pressure sensor signal, an ECG R-wave signal and an ECG P-wave signal.

Turning now to FIG. 3, there is depicted one embodiment of a pressure sensing circuit 11 that operatively couples to pacing circuitry resident in the IMD 14 illustrated in FIG. 2 and that is used for determining the hemodynamic status of a patient. It is to be understood that IMD 14 is contained within a hermetically-sealed, biologically inert outer shield or "can", in accordance with common practice in the art. The sensing circuit 11 is operable in conjunction with an implantable absolute pressure sensor 62 that is implanted in the patient's RV as depicted in FIG. 1 and couples pressure signal 412 to pressure sensing circuit 11. The IMD 14 includes pressure sensing circuit 11 as well as other circuitry as is well known to those of skill in the art.

Operation of the implantable medical device 14 will now be discussed in more detail with reference to FIGS. 4 and 5. As stated above, measurements of pressure developed, particularly pulmonary wedge pressure, inside the heart are typically used to determine the health of a patient and provide a proper therapy. One illustrative method for determining pulmonary artery and right arterial diastolic and systolic pressure begins with reference to the simplified block diagram of pressure sensing circuit 11 illustrated in FIG. 3. The basic functional components are differentiators 340, 342, comparators 336, 338, 344, sample-and-holds 332, 334, 346, 350, and delays 330, 348. Embodiment 11 also requires the output 314 from an R-wave sense amplifier and the output 316 from a P-wave sense amplifier, as known to those skilled in the art of cardiac pacing. Thus, the timing of the delivered cardiac stimulation and evoked (or intrinsic) response can readily be linked to developing pressure as measured by pressure sensing circuit 11 and as provided via signal 412.

Figure 4A:
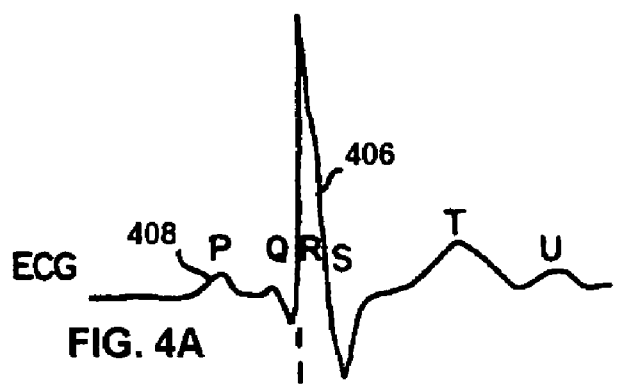
FIG. 4A illustrates a typical ECG signal.
Figure 4B:
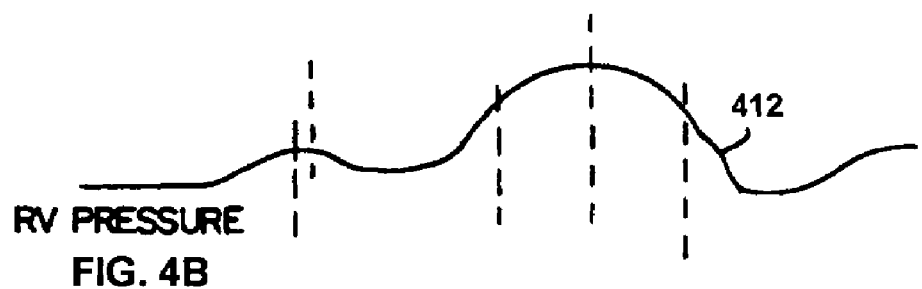
FIG. 4B illustrates a typical right ventricular pressure signal.
Figure 4C:
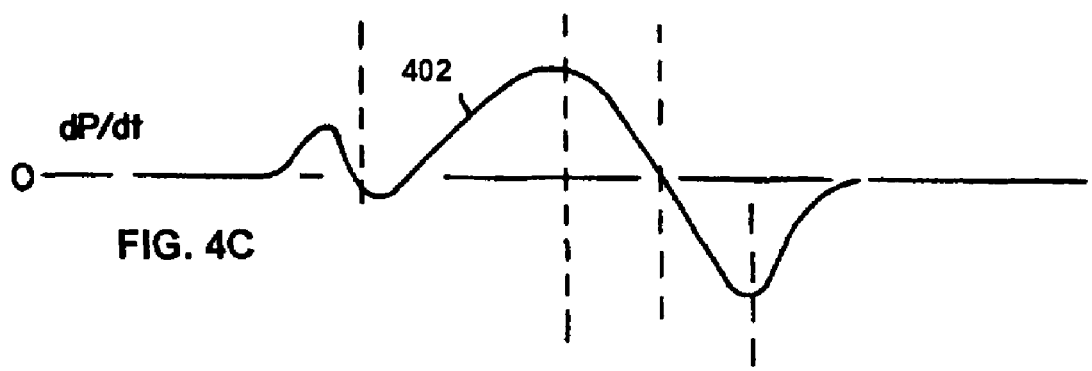
FIG. 4C illustrates a signal derived from the derivative of the signal depicted in FIG. 4B, and which can be used to determine pulmonary artery systolic pressure as well as right atrial systolic and diastolic pressure.

Operation of embodiment 11 shown in FIG. 3 begins by differentiating the signal 412 from an absolute pressure sensor 62 (FIG. 1) which is chronically implanted in the RV, to provide a first and a second derivative of the RV pressure signal (i.e., dP/dt and $d^2P/dt^2$ respectively). A typical ECG signal is illustrated in FIG. 4A while its associated right ventricular (RV) pressure sensor waveform 412 is shown in FIG. 4B. Differentiator 340 provides an output signal 402 illustrated in FIG. 4C that is the first derivative of waveform 412. Differentiator 342 provides an output signal 404 illustrated in FIG. 4D that is the second derivative of waveform 412. From these waveforms (and relates mathematical derivations) the PA diastolic pressure and PA systolic pressure are readily obtained. That is, as previously described PA diastolic pressure occurs when maximum positive rate-of-change of RV pressure occurs (upon opening of PA valve) and, PA systolic pressure occurs at maximum RV pressure (while the PA valve is still open).

FIG. 4A depicts a representative cardiac surface ECG waveform for a single cardiac cycle. The ECG reveals a P-wave 402 and an R-wave 404 that forms a portion of the QRS complex as well as a T-wave and a U-wave. Like other drawings contained herein, FIG. 4A is not rendered to scale; however, FIG. 4A more or less accurately represents a cardiac cycle during normal sinus rhythm (NSR) although the present invention is not limited to operation only during NSR. Inspection of the waveforms shown in FIGS. 4b–4D, which represent a waveform 412 from a direct measurement of RV pressure, a first derivative 402 of the RV pressure waveform 412, and a second derivative 404 of said RV pressure waveform 412, respectfully, it can be seen that the maximum RV (and PA) systolic pressure occurs the first time after the R-wave 406 that the first derivative waveform (dP/dt) 402 passes through zero (i.e., has a null value). It follows from the discussion above that the maximum dP/dt (corresponding to PA diastolic pressure) occurs when the waveform representing the first derivative 402 has a maximum positive value. This also corresponds to the first time after the R-wave 406 that the waveform representing the second derivative 404 transitions from a positive value to a negative value (i.e., has a null value). With reference to FIGS. 5A to 5C, these three drawings depict a temporal sequence of ventricular stimulation (VEGM 502) showing an R-wave evoked at 504 due to ventricular pacing stimulation, FIG. 5B depicts two waveform traces namely PA pressure 518 and RV pressure 412, and FIG. 5C depicts a waveform 506 representing the first derivative of the RV pressure 412 of FIG. 5B. In FIG. 5B, the PA diastolic pressure (i.e., ePAD) waveform is identified as aligned with the occurrence of maximum positive rate-of change of the RV pressure (i.e., $dP/dt_{max}$). Also depicted in FIG. 5B is the PA systolic pressure that corresponds to a null value of the first derivative of RV pressure and also corresponds to the maximum negative value of the second derivative of RV pressure (see e.g., FIG. 5C). Also depicted in FIG. 5C, the right atrial (RA) systolic pressure can be seen to align with a null value for the first derivative of the RV pressure signal that occurs prior to the occurrence of $dP/dt_{max}$. With reference again to FIG. 5B, representative waveforms of developing pulmonary artery (PA) pressure and right ventricular (RV) pressure are illustrated. From FIG. 5B it is readily apparent that PA diastolic pressure (minimum PA pressure) occurs at essentially the same moment when the PA pressure and RV pressure signals cross each other (i.e., when the PA valve opens during the maximum rate-of-change of RV pressure).

FIG. 5C is the dP/dt waveform 506 resulting from a first derivative of the patient's RV pressure signal 412. Again, note that the maximum positive amplitude of the dP/dt waveform 506 occurs at the same time that the PA pressure 518 equals the RV pressure 412. Also illustrated in FIG. 5C is that PA systolic pressure occurs at the approximate time that the first derivative equals a null value (corresponding to the top of the peak of an RV pressure waveform 412).

Figure 4D:
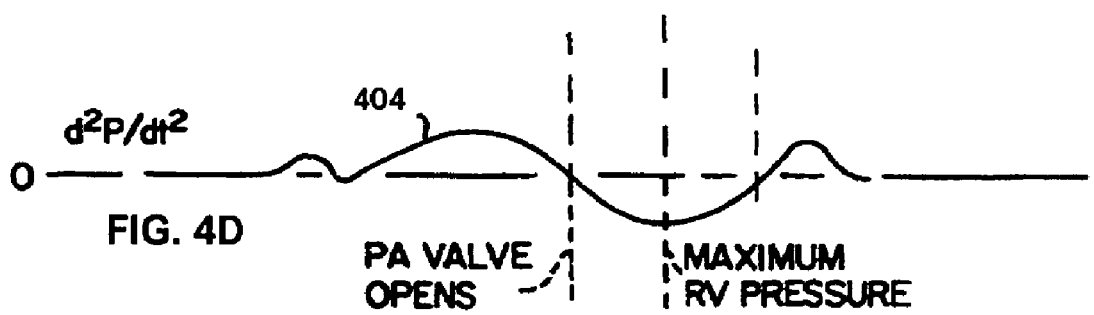
FIG. 4D illustrates a signal derived from the derivative of the signal depicted in FIG. 4C, and which can be used to determine pulmonary artery diastolic pressure.

Referring again to the simplified circuit diagram of pressure sensing circuit 11 depicted in FIG. 3 (and with reference to FIGS. 4A–4D), the PA systolic pressure 322 is determined by feeding the RV pressure sensor output 412 into a sample and hold circuit 334. The sample and hold circuit 334 is triggered by the sensing of the R-wave 406 shown in FIG. 4A. The systolic pressure 322 is then latched when the dP/dt waveform 402 illustrated in FIG. 4C goes negative (i.e., achieves a null value) as determined by comparator 336 output signal 328. This value of systolic pressure will be held until the next R-wave 406 is sensed, enabling the sample and hold circuit 334 to change values. Of course, a series of systolic pressure values may be read from the sample and hold circuit 334 and stored in an available memory location for later comparison or manual review in the context of the then-present operative pacing intervals. Similarly, the PA diastolic pressure is determined by feeding the RV pressure signal 412 into a sample and hold circuit 332 which is latched by comparator 338 the first time that the second derivative waveform 404, as illustrated in FIG. 4D, goes negative (i.e., achieves a null value) after a sensed R-wave 406. In this case, a short delay 330 in the pressure signal path balances the electronic delays in the two signal paths, keeping the timing synchronized.

The RA systolic pressure 324 and RA diastolic pressure 320 may also be derived according to the present invention. For RA systolic pressure 324, the RV pressure signal 412 is provided to sample and hold circuit 346 which is triggered upon detection of a P-wave by P-wave detection circuit 316. Comparator 344 latches the first time that the first derivative of RV pressure signal has a local positive maximum following detection of a P-wave (see FIG. 5C). For RA diastolic pressure 320, the RV pressure signal 412 is provided to sample and hold circuit 350 which, following a preprogrammed delay of approximately 100 ms is triggered upon detection of a P-wave by P-wave detection circuit 316. Sample and hold circuit 350 captures the RA diastolic pressure 320 following the ~100 ms delay when the first derivative of RV pressure signal transitions from a null value to a positive value following measurement of RA systolic pressure 324.

From the above description of the present invention, it is apparent that numerous pressure measurements (and derivatives and integrals thereof) and combinations thereof as described herein can be advantageously utilized according to the present invention. For example, the present invention may utilize right atrial or right ventricular pressure (e.g., systolic, diastolic, mean, etc.) and rate-of-change of same, including maximum or minimum (dP/dt), ePAD pressure, PA systolic and PA diastolic pressure, among others.

If required, measurement of atrial pressures can also be accomplished similarly to the RV pressure measurement techniques previously described, as follows. The right atrial (RA) systolic pressure 324, like PA systolic pressure 322, is latched by a sample and hold circuit 346. Unlike PA pressure measurements however, latching occurs the first time that the dP/dt waveform 402 passes through zero subsequent to detection of a P-wave 408 as depicted in FIG. 4A. The RA diastolic pressure 320 is determined in the preferred embodiment shown in FIG. 3 by latching the RV pressure 312 after a short time delay (e.g., 100 msec) before the RA systolic pressure 324 measurement of interest. This is accomplished by delaying the RV pressure signal 412 with a delay circuit 348, and then latching the delayed signal with a sample and hold circuit 350 upon detection of a p-wave 408.

Figure 6:
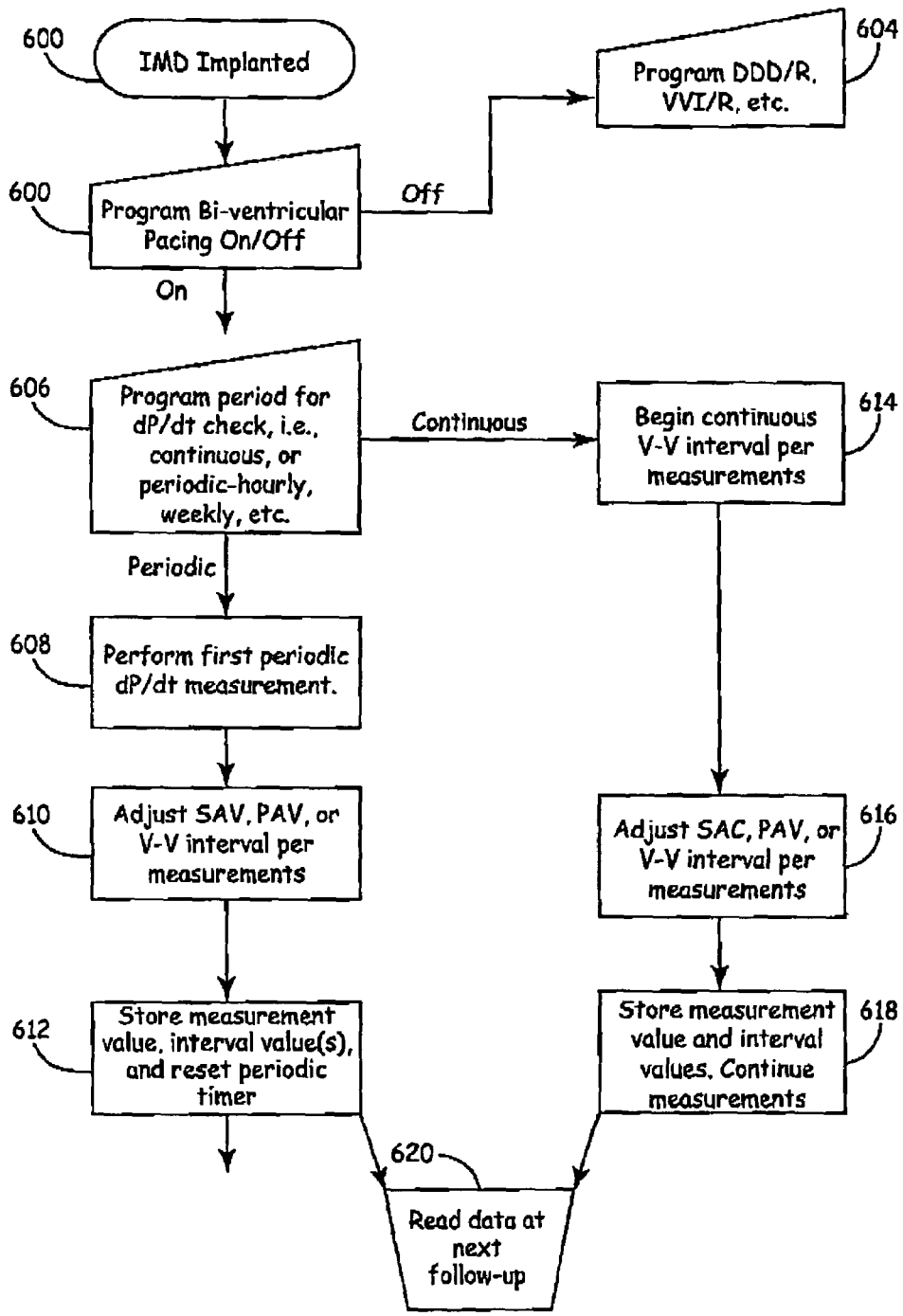
FIG. 6 is a flow chart illustrating the steps of periodically determining the $dP/dt_{max}$ and storing these data for use in adjusting one or more pacing delay intervals (e.g., A-V, A-A, V-V, PAV, SAV).

Turning now to FIG. 6, implantation of an IMD 14 occurs at step 600 on a given date and the attending physician, for one reason or another, may choose to delay programming of biventricular or CRT pacing and, instead programs the IMD 14 to an alternative mode 604. In most cases, however, the physician will program IMD to biventricular pacing 602 either at implant or post-implant prior to release from the hospital. At the time of programming biventricular pacing 602, the physician will be asked to program the desired frequency of pressure measurements at step 606. Continuous beat-for-beat measurement may be selected (at step 614) and according to this programming decision the pressure sensing circuit 11 (FIG. 3) measures developing cardiac pressure (and derivatives and/or integrals thereof for every cardiac cycle. According to the present invention, the operative timing circuitry within the IMD 14 iteratively adjusts one or more of the pacing intervals at step 616 (e.g., A-A, A-V, V-A, SAV, PAV, V-V, etc.) on an essentially continuous basis. The changes to the pacing interval(s) as well as the resultant pressure measurement values 618 are stored in IMD memory. These stored intervals and pressure values, along with the time or dates the measurements were taken (and changes to the intervals) are thus available to the physician for review at next follow-up 620.

If, however, the physician selects a periodic pressure measurement regime (e.g., hourly, daily, weekly, or monthly, etc.) at step 606, the IMD 14 will immediately begin measuring pressure at step 608 and will iteratively test various pacing intervals at step 610 and implement the optimal pacing intervals based on hemodynamic performance as revealed by the pressure measurements 610. The next iterative pressure measurement cycle will occur after a predetermined amount of time after a prior cycle, based on the period of time chosen by the physician at step 606. The pressure values (e.g., direct, mean, median, average, derivative and/or integral) from the periodic measurements and the values for a given set of pacing intervals, and the dates of any changes will be stored in device memory at step 612 and remain available for physician review at the next follow-up 620. Of course, while a LUT can be used to store the pacing interval set and corresponding hemodynamic data other computer readable storage medium may be used. For example, as is known to those of skill in the art, serial access memory (SAM) buffers, random access memory (RAM) including dynamic and static variants thereof (DRAM, SRAM), and read only memory (ROM) also known as "firmware," and programmable and electrically erasable programmable variants thereof (PROM, EEPROM also known as "flash memory") and the like may be successfully used in practicing the present invention. In addition to storing data as just described (i.e., a pacing interval set and the resultant hemodynamic data), other physiologic information may also be stored. For example, a resting condition heart rate, activity of daily living (ADL) condition heart rate, a sleeping condition heart rate, an upper tracking rate (UTR) condition heart rate, a lower tracking rate (LTR) condition heart rate, and the like may be stored in conjunction with the other stored data. Thus, a technique for initializing hemodynamic optimization according to the present invention involves providing multi-chamber cardiac pacing therapy to a patient at each one of a set of desired heart rates and measuring the resultant pressure development (and derivatives and/or integrals thereof) and storing same for comparison.

An information set of pacing intervals, heart rate and resulting hemodynamic metrics can be used in at least two ways. First, the set can be used in the event that a chronically-implanted pressure sensor and/or pressure sensing circuitry fails to provide a useful signal, drifts from a previously calibrated condition, is removed, or is otherwise unavailable. In such event, until such time as useful pressure sensor signals later become available or a clinical intervention can be convenient scheduled, the paced heart rate(s) can control which set of pacing intervals—that corresponding to the best hemodynamic response—are used for given heart rate(s). Second (and somewhat related to the first way), a discrete heart rate or heart rate range(s) may be used as a controlling variable for delivery of the pacing stimulation therapy with "confirmatory reference" to the then-presently measured pressure values. In this second situation, periodic comparison of a stored information set with current pressure measurements are used to confirm that the patient's hemodynamics are responding as previously measured. If a material deviation is found to exist between the stored information and the current hemodynamic response, a new iteration of pacing intervals could be performed and new hemodynamic responses recorded as previously described. In addition, the patient and/or the attending clinician may be notified, also as previously described. Of course, a significant decompensation event indicative of further deleterious cardiac remodeling in a heart failure patient could indicate an imminent heart failure hospitalization (HFH) event for the patient.

As previously described herein, during iterative cycling among different pacing interval sets a variety of pressure measurements are made and the resultant discrete direct pressure values (and any derived and/or integrals thereof) are stored in connection with the pacing intervals that produced the values. The pressure measurements are deemed to represent an evoked systemic hemodynamic state for the patient and, as such, after a new pacing interval set is implemented a settling period may beneficially provide a more accurate assessment of each such hemodynamic state. The measured pressures and related data reflective of a new hemodynamic state are compared and the most desirable hemodynamic state selected. Then, the pacing intervals that correspond to the most desirable hemodynamic state are programmed as operative parameters for the delivery of a multi-chamber cardiac stimulation therapy, such as CRT.

The present invention provides techniques and apparatus for utilizing more than one such pressure measurement (as well as mathematical derivatives and integrals thereof) so that optimally adapted hemodynamics result. In one embodiment of the present invention, a regime of periodic sampling pressure development is used. The periodic sampling may occur on the order of minutes, hours, minutes, days, weeks, etc. A reference fluid pressure as measured during nominal, or default, pacing interval settings for a given cardiac pacing device can be used as representative of a relatively stable hemodynamic state for a patient. The reference fluid pressure, and the subsequent iteratively derived sets of pacing intervals and hemodynamic data, may be measured on a beat-to-beat basis or over several cardiac cycles or over several minutes, and the like. The sampled fluid pressure values can be stored (e.g., in computer readable memory) along with the corresponding pacing time intervals used during sampling and any other related physiologic data. A convenience memory storage structure includes a look up table (LUT), although any similar memory structure may be used. Then one or more—or at least two—pacing time intervals are modified, then a period of time is preferably allowed to elapse to allow the hemodynamics to stabilize in response to the new pacing intervals, prior to again sampling the developed fluid pressure(s). This iterative sequence may be repeated for as many combinations of pacing intervals as desired by a clinician. Then, optionally for those cardiac pacing devices coupled to a so-called "activity sensor," additional rounds of measurements may be made while the patient exercises or otherwise increases heart rate to an elevated level above the resting heart rate used while the pacing intervals are varied and pressure(s) measured. Then, the stored array of pressure measurement and applicable timing intervals may be sent via telemetry for computerized analysis and/or manual review and the like. The IPG 14 then receives pacing interval programming resulting from the iterative sampling. Thus, an IPG 14 may be programmed to utilize one set of pacing timing intervals for a given heart rate or heart rate range or in response to a rapidly increasing or decreasing heart rate, and the like. For example, the IPG 14 may be programmed for relatively improved RV or RA systolic function while allowing adequate time for RV diastolic to decrease to a desired level (e.g., percentage of RV systolic pressure). Those of skill in the art will readily appreciate how to optimize one or more hemodynamic parameters of a patient given an apparent level of exertion and/or heart rate.

In addition to using heart rate, output from an activity sensor and the like, one may utilize injected direct current (dc) impedance measurements to gauge actual ventilation rate (e.g., minute ventilation) and/or a level of pulmonary edema (e.g., using one or more endocardial electrodes vectored to another or to a portion of the canister of IPG 14). This aspect of the present invention adds another dimension to the relationship between adjustable time intervals of an IPG 14 and the actual physiologic and hemodynamic state a patient.

Of course, as with most modern-day IPG units 14 a remote transmission/receiving station (not depicted) telemetrically coupled to the IPG 14 and/or a programmer for said IPG 14 may be configured to display all or any limited number of pacing interval data, hemodynamic data, physiologic data and the like. In addition to or in lieu of a bulky dedicated remote station, the remote station may comprise a portable unit that may accompany a patient and provide a relative or present hemodynamic index (or historical trend information) regarding a hemodynamic status of said patient. The patient could be notified of changes in said index or trend via a tactile or vibratory action of the remote station or IPG 14, a visual indication (e.g., numerical information, bar graphs, colored lines and/or LEDs, and the like), and/or an audible indication.

The sampled and stored blood pressure data are preferably absolute pressure values and do not account for changes in barometric pressure affecting the ambient pressure load on the pressure sensor module. Physicians typically measure blood pressure in relation to atmospheric pressure. Thus, it may be necessary to separately record atmospheric pressure data with separate measuring and recording equipment. At present, a separate, portable pressure recording unit (not shown) worn externally by the patient to record atmospheric pressure is contemplated to be used with the system of the present invention. The atmospheric pressure and a time and date tag are preferably recorded in the external unit at periodic, e.g. one minute, intervals. The atmospheric pressure data is intended to be read out from the external unit when the absolute pressure and optional other data stored in a RAM/ROM unit is telemetered out and the data correlated by time and date and employed by the physician to derive diagnoses of the patient's condition.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A method of hemodynamically optimizing pacing intervals in a cardiac stimulation therapy device that provides pacing therapy to at least three chambers of a heart, comprising: a) measuring developing fluid pressure with a pressure sensor adapted to be coupled to a cardiac chamber and providing a pressure signal therefrom for at least one cardiac cycle; b) storing at least a one of 1) the pressure signal or 2) a temporal derivative of the pressure signal, and a then-present pacing interval set used when the pressure signal was measured; c) changing at least two pacing intervals of said pacing interval set, and d) returning to step a) until each of the at least two pacing intervals have been changed; e) comparing the stored pressure signal or the temporal derivative of the pressure signal corresponding to said at least two pacing intervals to the stored pressure signal or the temporal derivative of the pressure signal corresponding to; and f) utilizing a present pacing interval set that includes the at least two pacing intervals that provided the most favorable pressure signal or temporal derivative of the pressure signal when compared in step e), wherein the pressure sensor comprises an absolute pressure sensor coupled to an ambient pressure reference unit.

2. A method according to claim 1, wherein the chamber is a right atrial chamber or a right ventricular chamber.

3. A method according to claim 1, wherein said pressure sensor is coupled to a pacing lead.

4. A method according to claim 1, wherein said pressure sensor is coupled to a defibrillation lead.

5. A method according to claim 1, wherein said pacing intervals comprise at least a one of: an A-A interval, an A-V interval, a V-A interval, a V-V interval, a sensed-AV interval, a paced-AV interval.

6. A method according to claim 1, wherein said pacing intervals include a paced heart rate value.

7. A method according to claim 1, wherein the pressure signal represents at least a one of: an ePAD metric, a pulse pressure metric, a right ventricular systolic pressure metric, a right atrial systolic pressure metric, a right ventricular diastolic pressure metric, a right atrial diastolic pressure metric.

8. An apparatus for hemodynamically optimizing pacing intervals in a multi-chamber cardiac stimulation therapy device that provides pacing therapy to at least three chambers of a heart, comprising: means for measuring developing fluid pressure with a pressure sensor adapted to be coupled to a cardiac chamber and providing a pressure signal therefrom for at least one cardiac cycle; means for storing at least a one of 1) the pressure signal or 2) a temporal derivative of the pressure signal, and a then-present pacing interval set used when the pressure signal was measured; means for changing at least two pacing intervals of said pacing interval set, and means for returning to the initial step until each of the at least two pacing intervals has been changed; means for comparing the stored pressure signal or the temporal derivative of the pressure signal corresponding to said at least two pacing intervals; and means for utilizing a present pacing interval set that includes the at least two pacing intervals that provided the most favorable pressure signal or temporal derivative of the pressure signal when compared by the means for comparing wherein the pressure sensor comprises an absolute pressure sensor.

9. An apparatus according to claim 8, wherein the chamber is a right atrial chamber or a right ventricular chamber.

10. An apparatus according to claim 8, wherein said pressure sensor is coupled to a pacing lead.

11. An apparatus according to claim 8, wherein said pressure sensor is coupled to a defibrillation lead.

12. An apparatus according to claim 8, wherein said pacing intervals comprise at least a one of: an A-A interval, an A-V interval, a V-A interval, a V-V interval, a sensed-AV interval, a paced-AV interval.

13. An apparatus according to claim 8, wherein said pacing intervals include a paced heart rate value.

14. An apparatus according to claim 8, wherein the pressure signal represents at least a one of: an ePAD metric, a pulse pressure metric, a right ventricular systolic pressure metric, a right atrial systolic pressure metric, a right ventricular diastolic pressure metric, a right atrial diastolic pressure metric.

15. A computer readable medium for storing instructions for performing a method of hemodynamically optimizing pacing intervals in a multi-chamber cardiac stimulation therapy device that provides pacing therapy to at least three chambers of a heart, comprising: instructions for measuring developing fluid pressure with a pressure sensor coupled to a cardiac chamber and providing a pressure signal therefrom for at least one cardiac cycle; instructions for storing at least a one of 1) the pressure signal or 2) a temporal derivative of the pressure signal, and a then-present pacing interval set used when the pressure signal was measured; instructions for chancing at least two pacing intervals of said pacing interval set; instructions for returning to the initial step until each of the at least two pacing intervals has been changed; instructions for comparing the stored pressure signal or the temporal derivative of the pressure signal corresponding to said at least two pacing intervals; and instructions for utilizing a present pacing interval set that includes the at least two pacing intervals that provided the most favorable pressure signal or temporal derivative of the pressure signal when compared in the comparing step, wherein the pressure sensor comprises an absolute pressure sensor.

16. A medium according to claim 15, wherein the pressure signal represents at least a one of: an ePAD metric, a pulse pressure metric, a right ventricular systolic pressure metric, a right atrial systolic pressure metric, a right ventricular diastolic pressure metric, a right atrial diastolic pressure metric.

17. A medium according to claim 15, wherein the chamber is a right atrial chamber or a right ventricular chamber.

* * * * *